(12) United States Patent
Kuroda

(10) Patent No.: US 6,650,727 B2
(45) Date of Patent: Nov. 18, 2003

(54) RADIATION TOMOGRAPHIC IMAGING APPARATUS AND METHOD

(75) Inventor: Yoshiyasu Kuroda, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 63 days.

(21) Appl. No.: 10/044,723

(22) Filed: Oct. 20, 2001

(65) Prior Publication Data

US 2002/0080910 A1 Jun. 27, 2002

(30) Foreign Application Priority Data

Dec. 15, 2000 (JP) ........................................ 2000-382668

(51) Int. Cl.[7] ................................................ A61B 6/00
(52) U.S. Cl. ............................................ 378/19; 378/4
(58) Field of Search ..................... 378/19, 8, 4, 901, 378/98.8, 21, 23

(56) References Cited

U.S. PATENT DOCUMENTS

| | | | | |
|---|---|---|---|---|
| 5,991,356 A | * | 11/1999 | Horiouchi et al. | 378/8 |
| 6,137,858 A | * | 10/2000 | Horiuchi | 378/19 |
| 6,215,843 B1 | * | 4/2001 | Saito et al. | 378/19 |
| 6,243,438 B1 | * | 6/2001 | Nahaliel et al. | 378/19 |
| 6,256,364 B1 | * | 7/2001 | Toth et al. | 378/4 |
| 6,289,075 B1 | * | 9/2001 | Marume | 378/8 |
| 6,370,218 B1 | * | 4/2002 | Toth et al. | 378/19 |

\* cited by examiner

Primary Examiner—Edward J. Glick
Assistant Examiner—Irakli Kiknadze
(74) Attorney, Agent, or Firm—Moonray Kojima

(57) ABSTRACT

A radiation tomographic imaging apparatus and method are provided in which the slice thickness can be dynamically switched during scanning, and the emission center of radiation can be arbitrarily moved in a direction of carrying a subject. There are provided an X-ray tube moving section 21 capable of moving the emission center of an X-ray tube 20 in a z-direction; a collimator 22 having an aperture whose openness can be adjusted, for forming the emitted X-rays into an X-ray beam 5 having a certain width and thickness to irradiate a desired region on a detector element array 23 with the X-ray beam 5; a data collecting section 24 for dynamically selecting or adding in varying combination the detected signal input supplied from the detector element rows in the detector element array 23 during scanning in response to a control signal CTL303; and a central processing apparatus 30 for changing the emission center of the X-ray tube 20, the openness of the aperture in the collimator 22, and the data to be collected by the data collecting section 24 corresponding to status information input via an input device 31.

18 Claims, 9 Drawing Sheets

RADIATION TOMOGRAPHIC IMAGING APPARATUS AND METHOD

BACKGROUND OF THE INVENTION

The present invention relates to a radiation tomographic imaging apparatus and method, and particularly to a radiation tomographic imaging apparatus and method for producing multi-slice tomographic images of a region through which a radiation beam having a width and a thickness passes.

RELATED ART

Known radiation tomographic imaging apparatuses include an X-ray CT (computed tomography) apparatus, for example, that employs X-rays for the radiation. In the X-ray CT apparatus, an X-ray tube is used for the X-ray generation.

The X-ray CT apparatus is configured to rotate a radiation emitting/detecting system, i.e., an X-ray emitting/detecting system, around a subject (to scan the subject); measure projection data of the subject by the X-rays in a plurality of view directions surrounding the subject; and produce (reconstruct) a tomographic image based on the projection data.

An X-ray emitting apparatus in the X-ray emitting/detecting system emits an X-ray beam having a width that encompasses a region to be imaged and a certain thickness in a direction perpendicular to the width.

The thickness of the X-ray beam can be varied by controlling the openness of an X-ray passing opening (aperture) in a collimator, and the slice thickness for one view can thus be adjusted.

An X-ray detecting apparatus in the X-ray emitting/detecting system detects X-rays by a multi-channel X-ray detector, in which a multiplicity of (e.g. ca. 1,000) X-ray detector elements are arranged in a linear array (which will be sometimes referred to as a detector element row hereinbelow) in the width direction of the X-ray beam.

The multi-channel X-ray detector has a length (i.e., a width) equal to the width of the X-ray beam in the width direction of the X-ray beam. It also has a length (i.e., a thickness) larger than the thickness of the X-ray beam in the thickness direction of the X-ray beam.

Such multi-channel X-ray detectors include one in which, for example, a plurality of the detector element rows are arranged side by side in the thickness direction of the X-ray beam (i.e., in a direction of carrying the subject into an X-ray irradiated space (the body axis direction)) so that the plurality of detector element rows simultaneously receive the X-ray beam.

Since such an X-ray detector can obtain all the X-ray detected signals for a plurality of slices in one scan, it is used as an X-ray detector for performing a multi-slice scan with good efficiency.

In such an X-ray detector, each X-ray detector element row is configured to have a thickness (the length in the thickness direction of the X-ray beam) equal to a minimum slice thickness (e.g. 1 mm), and several to several tens, for example, of such rows are arranged side by side in the thickness direction of the X-ray beam so that the signals detected by the X-ray detector element rows can be arbitrarily combined in channels having the same index.

In the X-ray CT apparatus comprising such an X-ray detector, a multi-slice scan is performed simultaneously for three slices each having a slice thickness of 1 mm, by using the central three detector element rows, for example.

Alternatively, a multi-slice scan is performed simultaneously for three slices each having a slice thickness of 2 mm, by using the central six detector element rows to form three sets of detector element rows by combining adjacent row pairs.

Similarly, a multi-slice scan is performed simultaneously for a plurality of slices each having a different thickness, by using a number of detector element rows, the number being equal to the product of the slice thickness and the number of slices, and combining signals of a number of adjacent detector element rows, the number being equal to the slice thickness, to form a number of sets of detector element rows, the number being equal to the number of slices.

Although the conventional radiation tomographic imaging apparatus such as the X-ray CT apparatus is capable of varying the slice thickness as described above, however, the tomographic imaging is performed with the slice thickness fixed at a prespecified value during scanning, and the slice thickness cannot be dynamically switched during scanning.

Moreover, in the conventional radiation tomographic imaging apparatus, a portion near the center of the whole set of detector element rows in the X-ray detector is commonly used and portions nearer the sides are not used.

In other words, the conventional radiation tomographic imaging apparatus does not enable intentional movement of the radiation emission center in the direction of carrying the subject rested on the cradle into the radiation irradiated space (generally, in the body axis direction of the subject).

Since the slice thickness cannot be dynamically switched during scanning and the radiation emission center cannot be arbitrarily moved in the body axis direction of the subject in the radiation tomographic imaging apparatus for performing a multi-slice scan, the following disadvantage arises in performing, for example, CT fluoro (fluorography) imaging.

In order to perform the CT fluoro imaging, the subject rested on the cradle must be accurately positioned in the X-ray irradiated space, and a needle must be inserted into the subject to reach a site to be examined.

In inserting the needle, it can be confirmed by CT with certainty that the tip of the needle reached the site to be examined; however, when the position of the subject rested on the cradle is shifted due to the subject's body motion in the conventional radiation tomographic imaging apparatus, the cradle must be moved in a direction of carrying the cradle into the X-ray irradiated space or in the opposite direction for fine adjustment of the position, and the subject may be endangered when, for example, the needle has been inserted.

SUMMARY OF THE INVENTION

The present invention was made in the light of these circumstances, and has an object to provide a radiation tomographic imaging apparatus and method in which the slice thickness can be dynamically switched during scanning, and the radiation emission center can be arbitrarily moved in a direction of carrying a subject, thereby enabling tomographic imaging with safety and high accuracy.

In order to attain such an object, a radiation tomographic imaging apparatus in a first aspect of the present invention comprises: radiation emitting means capable of emitting a radiation beam and capable of changing a range irradiated by the radiation beam in response to a control signal; a detector element array comprising a plurality of radiation detector elements with their irradiated surfaces facing in an impinging direction of the radiation beam, in which array the radiation detector elements are arranged in one of two mutually perpendicular directions to form a detector element row, and a plurality of the detector element rows are arranged side by side in the other of the two mutually perpendicular directions; control means for receiving irradiated range information and outputting the control signal to the radiation emitting means corresponding to the information; and tomographic image producing means for producing multi-slice tomographic images of a region through which the radiation beam passes based on radiation detected signals for a plurality of views detected by the detector element array corresponding to the irradiated range information.

Moreover, in the first aspect of the present invention, the radiation tomographic imaging apparatus further comprises rotating means for rotating the radiation emitting means and detector element array around a subject carried into a radiation irradiated space.

Furthermore, in the first aspect of the present invention, the radiation tomographic imaging apparatus further comprises display means for displaying the tomographic images produced by the tomographic image producing means.

A radiation tomographic imaging apparatus in a second aspect of the present invention comprises: radiation emitting means capable of emitting a radiation beam and capable of changing a range irradiated by the radiation beam in response to a first control signal; a detector element array comprising a plurality of radiation detector elements with their irradiated surfaces facing in an impinging direction of the radiation beam, in which array the radiation detector elements are arranged in one of two mutually perpendicular directions to form a detector element row, and a plurality of the detector element rows are arranged side by side in the other of the two mutually perpendicular directions; data collecting means for collecting desired data by selecting or variedly combining detected signals from the detector element rows in the detector element array in response to a second control signal; control means for receiving irradiated range information and outputting the first control signal to the radiation emitting means and the second control signal to the data collecting means corresponding to the information; and tomographic image producing means for producing multi-slice tomographic images of a region through which the radiation beam passes based on radiation detected signals for a plurality of views detected by the detector element array corresponding to the irradiated range information and collected by the data collecting means.

Moreover, in the second aspect of the present invention, the radiation tomographic imaging apparatus further comprises rotating means for rotating the radiation emitting means and detector element array around a subject carried into a radiation irradiated space.

Furthermore, in the second aspect of the present invention, the radiation tomographic imaging apparatus further comprises display means for displaying the tomographic images produced by the tomographic image producing means.

In addition, in the second aspect of the present invention, the data collecting means comprises switching means for collecting desired data by selecting or variedly combining detected signals from the detector element rows in the detector element array in response to the second control signal; and converting means for converting the data from the switching means into digital data and outputting the digital data to the tomographic image producing means.

Besides, in the second aspect of the present invention, the data collecting means comprises converting means for converting the detected signals from the detector element rows in the detector element array into digital data; and switching means for collecting desired data by selecting or variedly combining the digital data from the converting means in response to the second control signal and outputting the data to the tomographic image producing means.

A radiation tomographic imaging apparatus in a third aspect of the present invention comprises: a radiation tube for emitting radiation; a collimator capable of forming the radiation emitted by the radiation tube into a radiation beam to emit the radiation beam and capable of changing a range irradiated by the radiation beam in response to a first control signal; a detector element array comprising a plurality of radiation detector elements with their irradiated surfaces facing in an impinging direction of the radiation beam, in which array the radiation detector elements are arranged in one of two mutually perpendicular directions to form a detector element row, and a plurality of the detector element rows are arranged side by side in the other of the two mutually perpendicular directions; radiation tube moving means capable of moving an emission center of the radiation tube in the other of the two mutually perpendicular directions in response to a second control signal; control means for receiving radiation irradiated range information and outputting the first control signal to the collimator and the second control signal to the radiation tube moving means corresponding to the information; and tomographic image producing means for producing multi-slice tomographic images of a region through which the radiation beam passes based on radiation detected signals for a plurality of views detected by the detector element array corresponding to the irradiated range information.

Moreover, in the third aspect of the present invention, the radiation tomographic imaging apparatus further comprises rotating means for rotating the radiation tube, collimator and detector element array around a subject carried into a radiation irradiated space.

Furthermore, in the third aspect of the present invention, the radiation tomographic imaging apparatus further comprises display means for displaying the tomographic images produced by the tomographic image producing means.

A radiation tomographic imaging apparatus in a fourth aspect of the present invention comprises: a radiation tube for emitting radiation; a collimator capable of forming the radiation emitted by the radiation tube into a radiation beam to emit the radiation beam and capable of changing a range irradiated by the radiation beam in response to a first control signal; a detector element array comprising a plurality of radiation detector elements with their irradiated surfaces facing in an impinging direction of the radiation beam, in which array the radiation detector elements are arranged in one of two mutually perpendicular directions to form a detector element row, and a plurality of the detector element rows are arranged side by side in the other of the two mutually perpendicular directions; radiation tube moving means capable of moving an emission center of the radiation tube in the other of the two mutually perpendicular directions in response to a second control signal; data collecting means for collecting desired data by selecting or variedly combining detected signals from the detector element rows in the detector element array in response to a third control signal; control means for receiving radiation irradiated range information and outputting the first control signal to the collimator, the second control signal to the radiation tube moving means and the third control signal to the data collecting means corresponding to the information; and tomographic image producing means for producing multi-slice tomographic images of a region through which the radiation beam passes based on radiation detected signals for a plurality of views detected by the detector element array corresponding to the irradiated range information and collected by the collecting means.

Moreover, in the fourth aspect of the present invention, the radiation tomographic imaging apparatus further comprises rotating means for rotating the radiation tube, collimator and detector element array around a subject carried into a radiation irradiated space.

Furthermore, in the fourth aspect of the present invention, the radiation tomographic imaging apparatus further comprises display means for displaying the tomographic images produced by the tomographic image producing means.

In addition, in the fourth aspect of the present invention, the data collecting means comprises switching means for collecting desired data by selecting or variedly combining detected signals from the detector element rows in the detector element array in response to the third control signal; and converting means for converting the data from the switching means into digital data and outputting the digital data to the tomographic image producing means.

Besides, in the fourth aspect of the present invention, the data collecting means comprises converting means for converting the detected signals from the detector element rows in the detector element array into digital data; and switching means for collecting desired data by selecting or variedly combining the digital data from the converting means in response to the third control signal and outputting the data to the tomographic image producing means.

A radiation tomographic imaging method in a fifth aspect comprises the steps of: emitting radiation onto a first range in a detector element array comprising a plurality of radiation detector elements with their irradiated surfaces facing in an emission direction of the radiation beam, in which array the radiation detector elements are arranged in one of two mutually perpendicular directions to form a detector element row, and a plurality of the detector element rows are arranged side by side in the other of the two mutually perpendicular directions; producing multi-slice tomographic images of the first range irradiated by the radiation beam based on radiation detected signals for a plurality of views detected by the detector element array; emitting radiation onto a second range smaller than the first range in the detector element array; and producing multi-slice tomographic images of the second range irradiated by the radiation beam based on radiation detected signals for a plurality of views detected by the detector element array.

According to the present invention, irradiated range information is input via, for example, an input device, and is supplied to the control means.

The control means receives the irradiated range information, generates a control signal corresponding to the information, and outputs the control signal to the radiation emitting means.

The radiation emitting means emits a radiation beam to a desired region on the detector element array using a range corresponding to the control signal.

Then, the tomographic image producing means produces multi-slice tomographic images of a region through which the radiation beam passes based on radiation detected signals for a plurality of views detected by the detector element array corresponding to the irradiated range information. The tomographic images are displayed on, for example, the display means.

As described above, according to the present invention, the slice thickness can be dynamically switched during scanning, and the focus of the radiation can be arbitrarily moved in a direction of carrying the subject. Therefore, an advantage that tomographic imaging can be performed with safety and high accuracy can be obtained.

Further objects and advantages of the present invention will be apparent from the following description of the preferred embodiments of the invention as illustrated in the accompanying drawings.

DETAILED DESCRIPTION OF THE INVENTION

Embodiments of the present invention will now be described in detail with reference to the accompanying drawings.

First Embodiment

Figure 1:
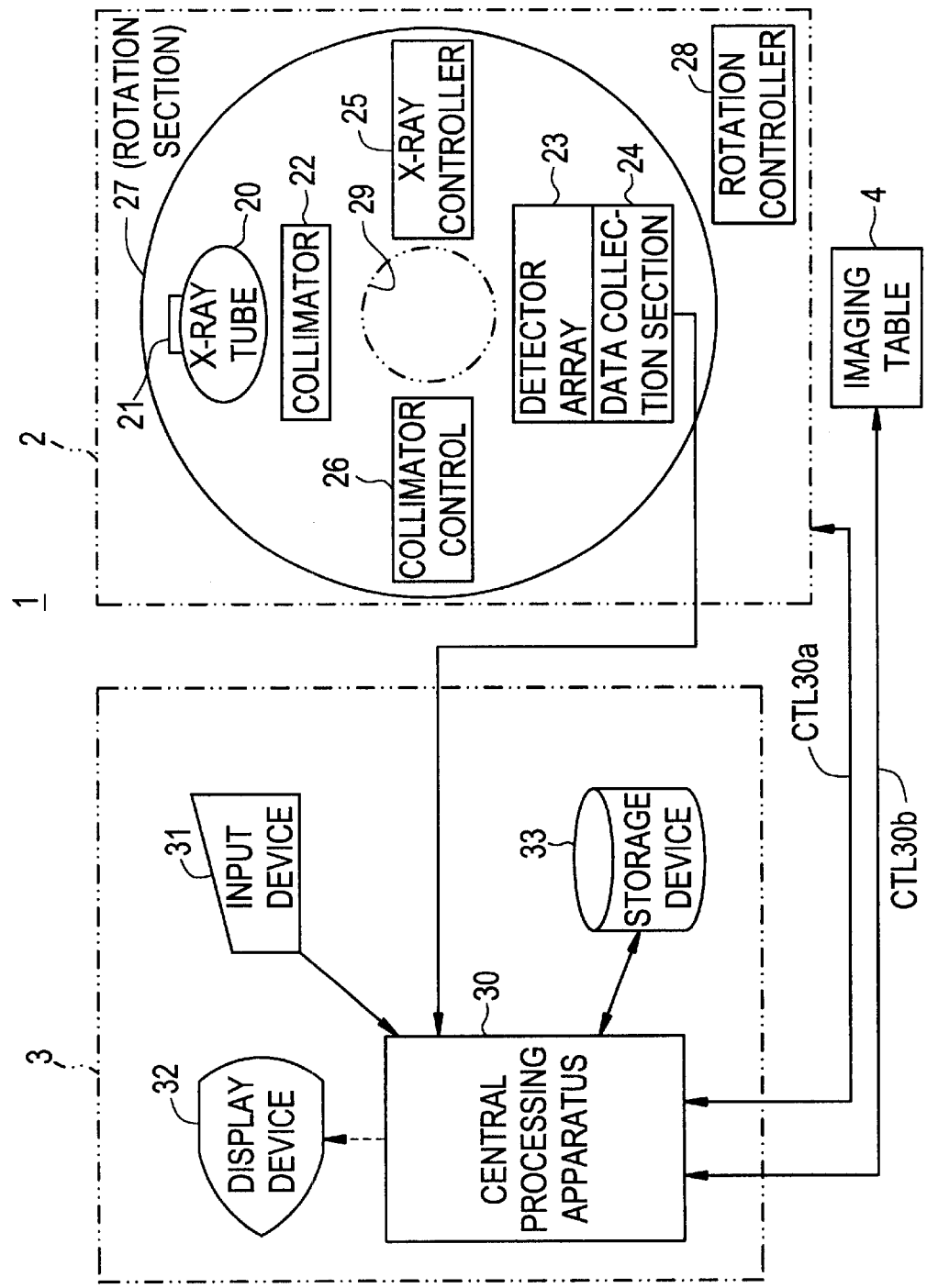
FIG. 1 is a block diagram showing the overall configuration of an X-ray CT apparatus that serves as the radiation tomographic imaging apparatus in accordance with the present invention.
Figure 2:
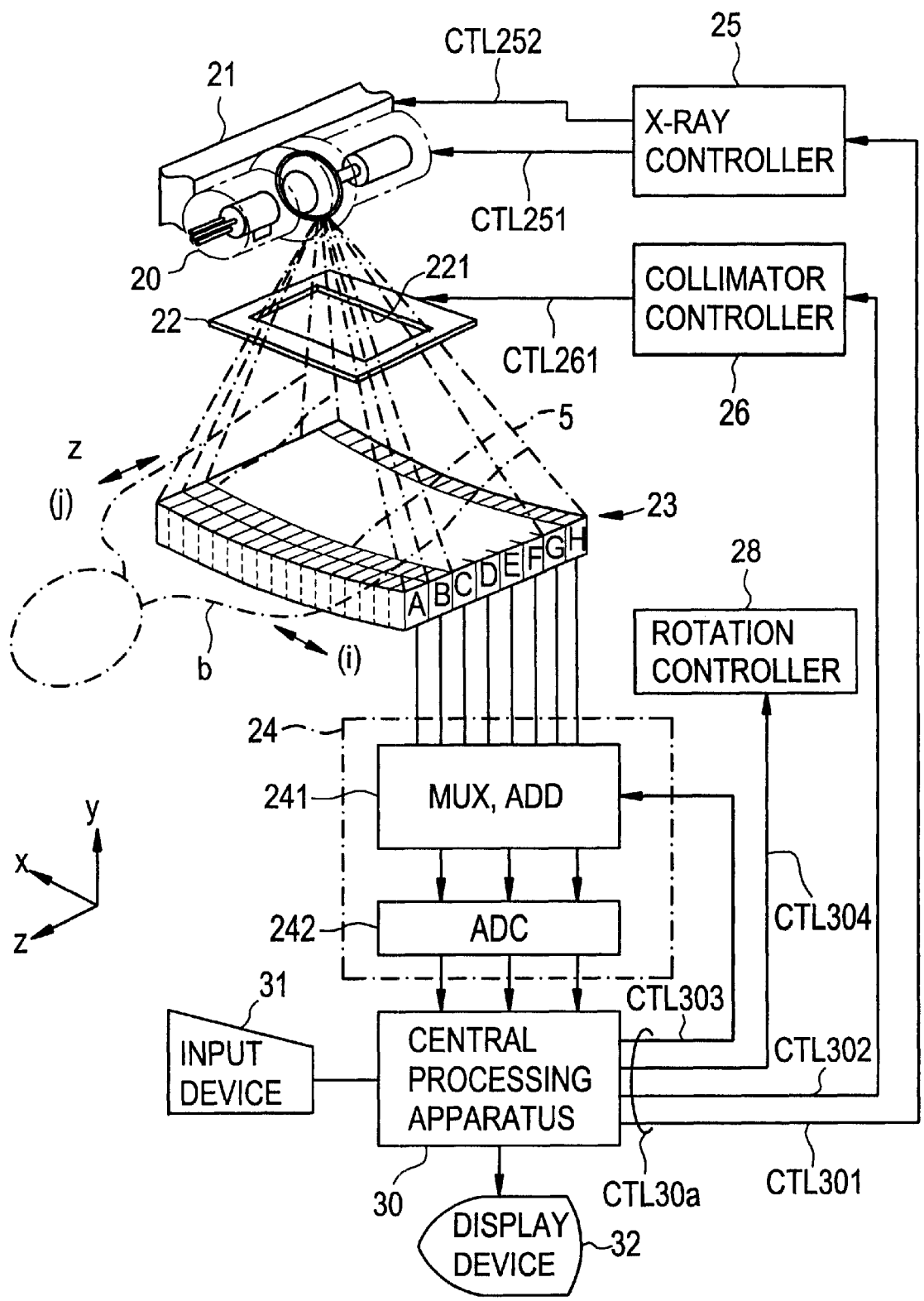
FIG. 2 is a system configuration diagram showing a first embodiment of the main portion of an X-ray CT apparatus that serves as the radiation tomographic imaging apparatus in accordance with the present invention.

FIG. 1 is a block diagram showing the overall configuration of an X-ray CT apparatus that serves as the radiation tomographic imaging apparatus in accordance with the present invention, and FIG. 2 is a system configuration diagram showing a first embodiment of the main portion of an X-ray CT apparatus that serves as the radiation tomographic imaging apparatus in accordance with the present invention.

The X-ray CT apparatus 1 comprises a scan gantry 2, an operating console 3 and an imaging table (cradle) 4, as shown in FIG. 1.

The scan gantry 2 comprises, as its main components, an X-ray tube 20, an X-ray tube moving section 21, a collimator 22, a detector element array 23, a data collecting section 24, an X-ray controller 25, a collimator controller 26, a rotating section 27 and a rotation controller 28.

Among these components, the X-ray tube 20, collimator 22, X-ray controller 25 and collimator controller 26 constitute the radiation emitting means in accordance with the present invention.

The X-ray tube 20 emits X-rays of predefined intensity towards the collimator 22 based on a control signal CTL251 from the X-ray controller 25.

The X-ray tube moving section 21 moves the position of the X-ray tube 20, particularly an emission center of the X-ray tube 20, in a direction of carrying the imaging table 4 for resting a subject into and out of an X-ray irradiated space 29 in the scan gantry 2 (i.e., a direction orthogonal to the drawing plane of FIG. 1, which will be sometimes referred to as a z-direction hereinbelow, as shown in FIG. 2), in response to a control signal CTL252 from the X-ray controller 25 by a distance corresponding to the command of the control signal CTL252.

The X-ray tube moving section 21 normally keeps the emission center of the X-ray tube 20 at a position that corresponds to the central portion of the detector element array 23 in the z-direction.

The collimator 22 forms the X-rays emitted by the X-ray tube 20 into a fan-shaped X-ray beam 5, i.e., a fan beam, having a certain width and a certain thickness (a slice thickness) based on a control signal 261 from the collimator controller 26, to irradiate a desired region on the detector element array 23 with the fan beam.

The thickness of the X-ray beam 5 is defined by openness control over an aperture 221 in the collimator 22 based on the control signal 261.

The openness control over the aperture 221 in the collimator 22 is dynamically switched to have an arbitrary width during scanning (i.e., during rotation of the rotating section 27), by the collimator controller 26 in response to a control command from a central processing apparatus 30 contained in the operating section 3, which will be described later.

The detector element array 23 comprises X-ray detector elements that serve as radiation detecting elements. The X-ray detecting elements are arranged in an array (matrix) in directions of the width (x-direction) and the thickness (z-direction) of the fan-shaped X-ray beam 5 as defined by the collimator 22.

Figure 3:
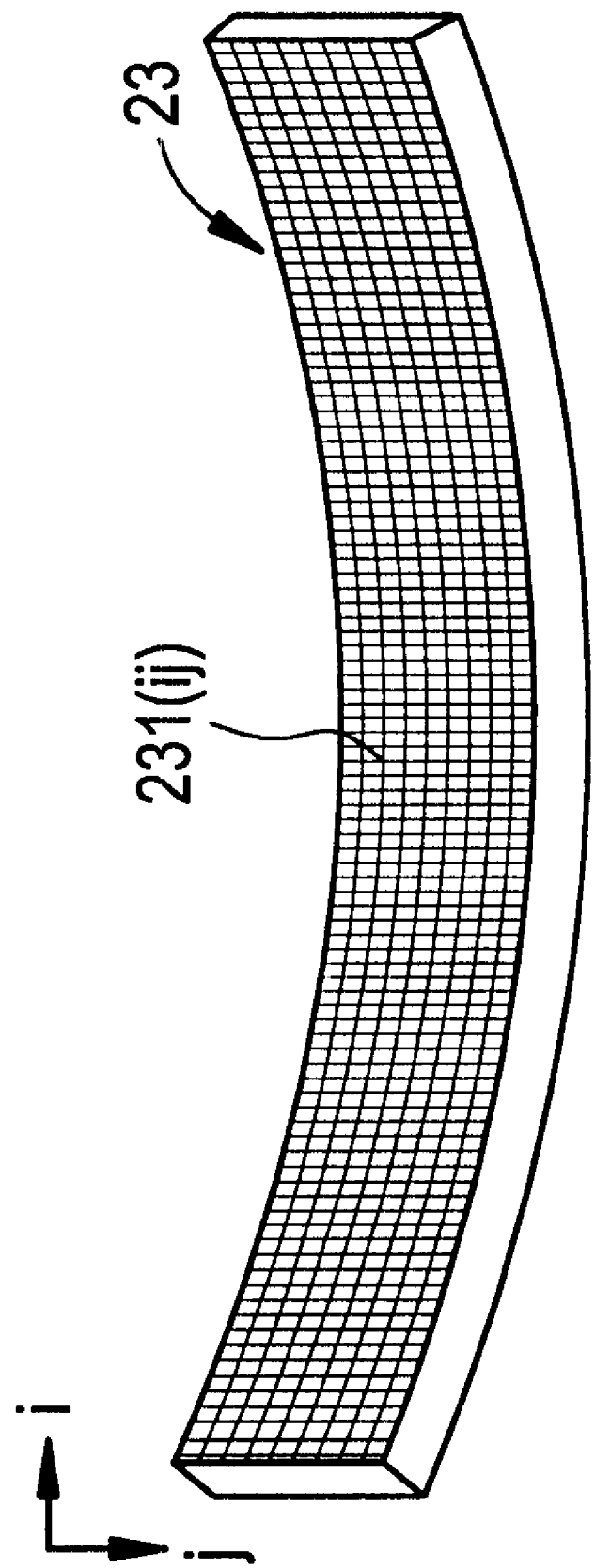
FIG. 3 schematically shows an example of configuration of a detector element array in accordance with the present invention.

FIG. 3 shows exemplary configuration of the detector element array 23 in accordance with the present invention.

The detector element array 23 is configured as a multi-channel, multi-row X-ray detector in which a plurality of (i×j) X-ray detector elements 231(i, j) are arranged in an i×j array (matrix) in a two-dimensional manner, as shown in FIG. 3.

The plurality of X-ray detector elements 231(i, j) arranged in a two-dimensional manner form an X-ray impinging surface curved to have a cylindrical concave surface in its entirety.

The symbol 'i' refers to a channel index, and, for example, i=1–1,000. The symbol 'j' refers to a row index, and, for example, j=1–16; however, in this embodiment, 'j' is defined as not less than four, for example, eight, in order to achieve a multi-slice scan. An example in which the number of rows is eight is shown in FIG. 2, and the rows are designated by symbols A–H.

Each of the X-ray detector elements 231(i, j) is constructed by a combination of a scintillator and a photodiode, for example.

However, the X-ray detector elements 231(i, j) are not limited to such a combination, but may be semiconductor X-ray detector elements using, for example, cadmium-tellurium (CdTe), or ion chamber type X-ray detector elements using xenon (Xe) gas.

The X-ray detector elements 231(i, j) having the same row number 'j' constitute a detector element row. A plurality of detector element rows are arranged side by side in parallel to one another.

Figure 4A:
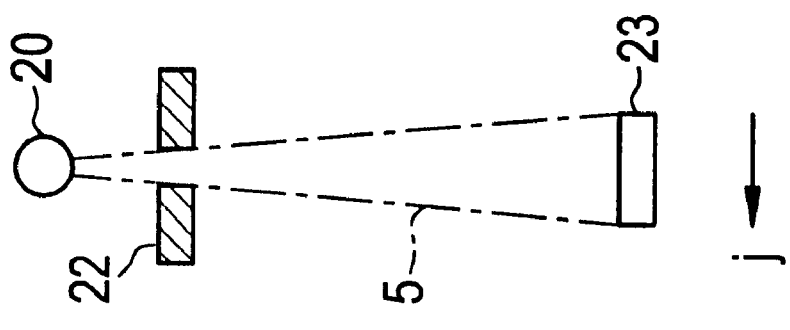
FIG. 4 shows the mutual relationship among an X-ray tube, a collimator and a detector element array in accordance with the present invention.
Figure 4B:
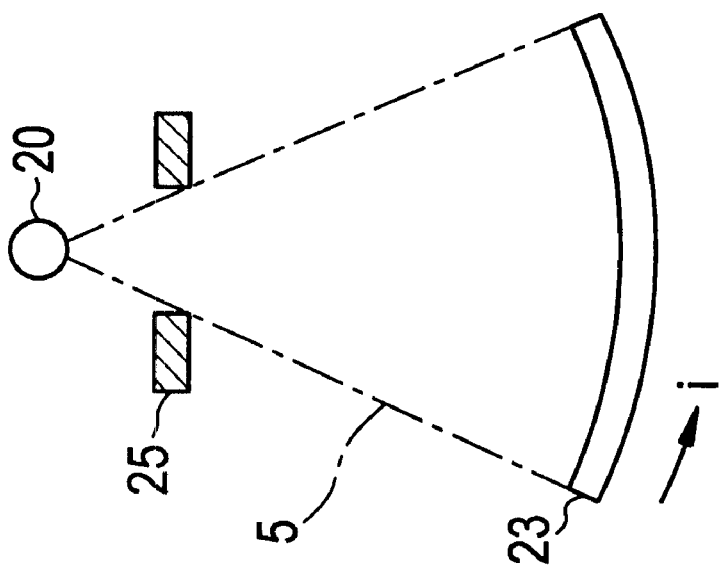

FIG. 4 shows the mutual relationship among the X-ray tube 20, collimator 22 and detector element array 23 in accordance with the present invention. FIG. 4(a) is a view from the front (in the z-direction) and FIG. 4(b) is a view from the side (in the x-direction).

As shown FIGS. 4(a) and (b), X-rays emitted by the X-ray tube 20 are formed into the fan-shaped X-ray beam 5 by the collimator 22, and the fan-shaped X-ray beam 5 impinges upon the detector element array 23.

FIG. 4(a) shows the extent of the fan-shaped X-ray beam 5, i.e., the width of the X-ray beam 5. The width direction of the X-ray beam 5 coincides with a direction of channel arrangement (i-direction) in the detector element array 23.

FIG. 4(b) shows the thickness of the X-ray beam 5. The thickness direction of the X-ray beam 5 coincides with a direction of detector element row arrangement (j-direction) in the detector element array 23.

Figure 5:
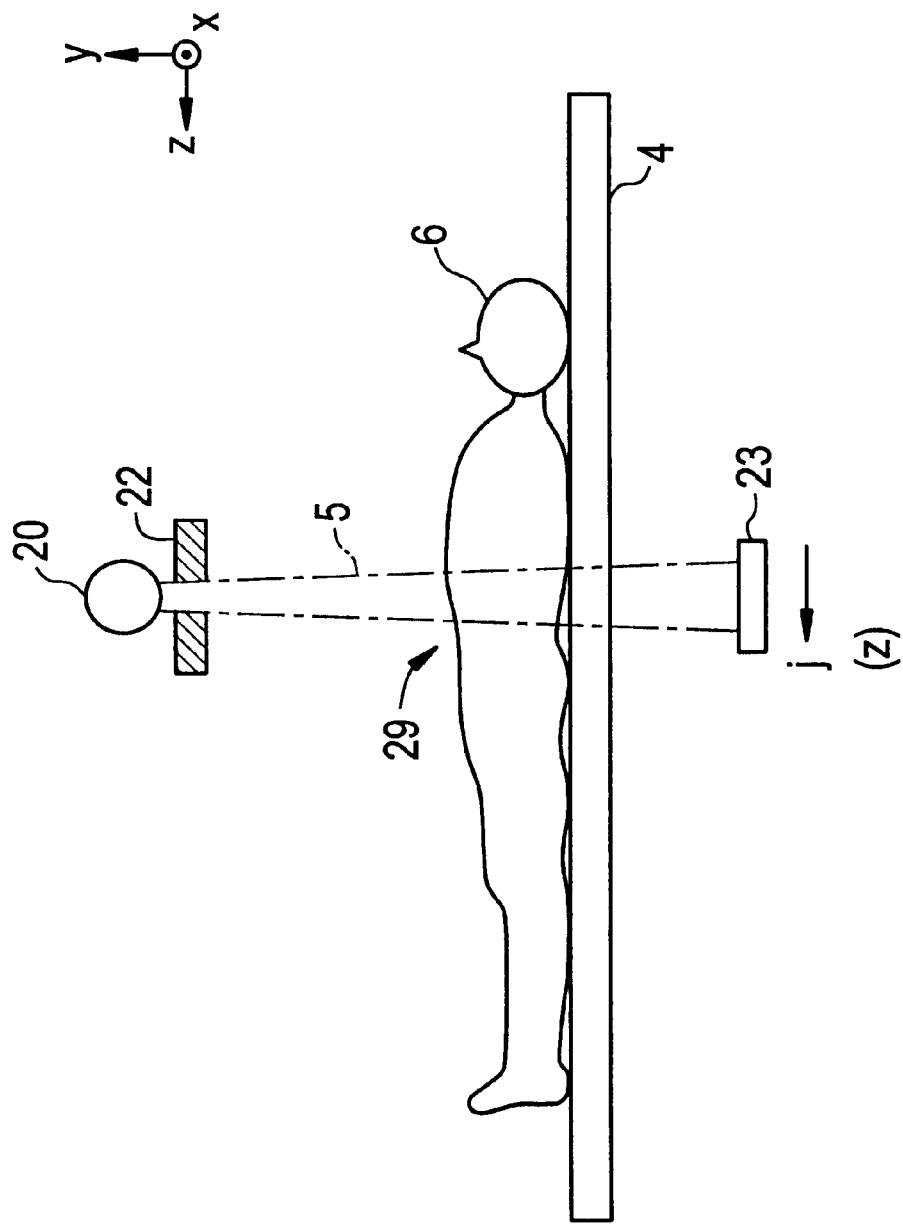
FIG. 5 is a view for explaining a mutual relationship among an X-ray tube, a collimator, a detector element array and a subject in accordance with the present invention.

A subject 6 rested on the imaging table 4 is carried into the X-ray irradiated space 29, as exemplarily shown in FIG. 5, with the subject's body axis intersecting the fan plane of the X-ray beam 5.

Thus, a projection image of the subject 6 sliced by the X-ray beam 5 is projected onto the detector element array 23.

The thickness of the X-ray beam 5 applied to the subject 6 is defined by the openness control over the aperture 221 in the collimator 22, as described above.

The data collecting section 24 collects data detected by the individual X-ray detector elements 231(i, j) in the detector element array 23, and outputs the detected data to the operating console 3.

The data collecting section 24 is comprised of a selection/addition switching circuit (MUX, ADD) 241 and an analog-digital converter (ADC) 242, as exemplarily shown in FIG. 2.

The selection/addition switching circuit 241 dynamically selects or adds in varying combination the detected signals input supplied from the detector element rows (e.g., eight rows (A–H)) in the detector element array 23 during scanning, in response to a control signal (third control signal) CTL303 from the central processing apparatus 30 in the operating console 3, which will be described later, and outputs the result to the ADC 242.

The ADC 242 converts the detected signals selected or added in arbitrary combination at the selection/addition switching circuit 241 in an analog signal form into digital signals, and outputs the digital signals to the central processing apparatus 30 in the operating console 3.

The X-ray controller 25 outputs the control signal CTL251 to the X-ray tube 20 to control the X-ray emission, in response to a control signal CTL301 from the central processing apparatus 30 in the operating console 3.

Moreover, the X-ray controller 25 outputs the control signal CTL252 to the X-ray tube moving section 21 to move the position of the X-ray tube 20, i.e., the emission center of the X-ray tube 20, in the direction of carrying the imaging table 4 for resting the subject into and out of the X-ray irradiated space 29 in the scan gantry 2 (i.e. the z-direction), in response to the control signal (second control signal) CTL301 from the central processing apparatus 30 in the operating console 3 by a commanded distance.

Furthermore, the X-ray controller 25 normally keeps the X-ray tube moving section 21 at a position such that the emission center of the X-ray tube 20 corresponds to the central portion of the detector element array 23 in the z-direction.

The collimator controller 26 outputs the control signal CTL261 to the collimator 22 to adjust the openness of the aperture 221 in the collimator 22, in response to a control signal (first control signal) CTL302 from the central processing apparatus 30 in the operating console 3, thereby forming the X-rays emitted by the X-ray tube 20 into the fan-shaped X-ray beam 5 having a commanded width and thickness (slice thickness) to irradiate a desired region on the detector element array 23 with the X-ray beam 5.

The rotating section 27 rotates in a certain direction based on a control signal CTL28 from the rotation controller 28. On the rotating section 27 are mounted the X-ray tube 20, X-ray tube moving section 21, collimator 22, detector element array 23, data collecting section 24, X-ray controller 25 and collimator controller 26, and these components change their positional relationship with respect to the subject 6 carried into the X-ray irradiated space 29 as the rotating section 27 rotates.

The rotation controller 28 outputs the control signal CTL28 to the rotating section 27 to rotate the rotating section 27 a desired number of times in a certain direction, in response to a control signal CTL304 from the central processing apparatus 30 in the operating section 3.

The operating section 3 comprises, as its major components, the central processing apparatus 30 that serves as the control means and the tomographic image producing image, an input device 31, a display device 32 and a storage device 33.

The central processing apparatus 30 is comprised of, for example, a microcomputer, and outputs a control signal CTL30b to the imaging table 4 for causing the imaging table 4 for resting the subject 6 to be carried into and out of the X-ray irradiated space 29 in the scan gantry 2 in the z-direction, in response to a command input via the input device 31.

The central processing apparatus 30 outputs the control signal CTL304 to the rotation controller 28 in the scan gantry 2 in response to a command, for example, a command to start a multi-slice scan, input via the input device 31, for causing the rotating section 27 in the scan gantry 2 on which the X-ray tube 20, X-ray tube moving section 21, collimator 22, detector element array 23, data collecting section 24, X-ray controller 25 and collimator controller 26 are mounted, to rotate a commanded number of times in a certain direction.

The central processing apparatus 30 also outputs the control signal CTL301 to the X-ray controller 25 for causing the X-ray tube 20 in the scan gantry 2 to emit X-rays.

Moreover, in response to status information that serves as the irradiated range information for defining the slice thickness input via the input device 31, the central processing apparatus 30 outputs the control signal CTL301 to the X-ray controller 25 for moving the emission center of the X-ray tube 20 in the direction of carrying the imaging table 4 for resting the subject into and out of the X-ray irradiated space 29 in the scan gantry 2 (i.e. the z-direction) by a commanded distance; and outputs the control signal 302 to the collimator controller 26 for causing the collimator 22 to emit the X-ray beam 5 with a certain openness.

Furthermore, the central processing apparatus 30 outputs the control signal CTL303 to the selection/addition switching circuit 241 in the data collecting section 24 in response to the status information for defining the slice thickness input via the input device 31 so that the selection/addition switching circuit 241 dynamically selects or adds in varying combination the detected signal input supplied from the detector element rows (e.g., eight rows (A–H)) in the detector element array 23 during scanning.

Figure 6:
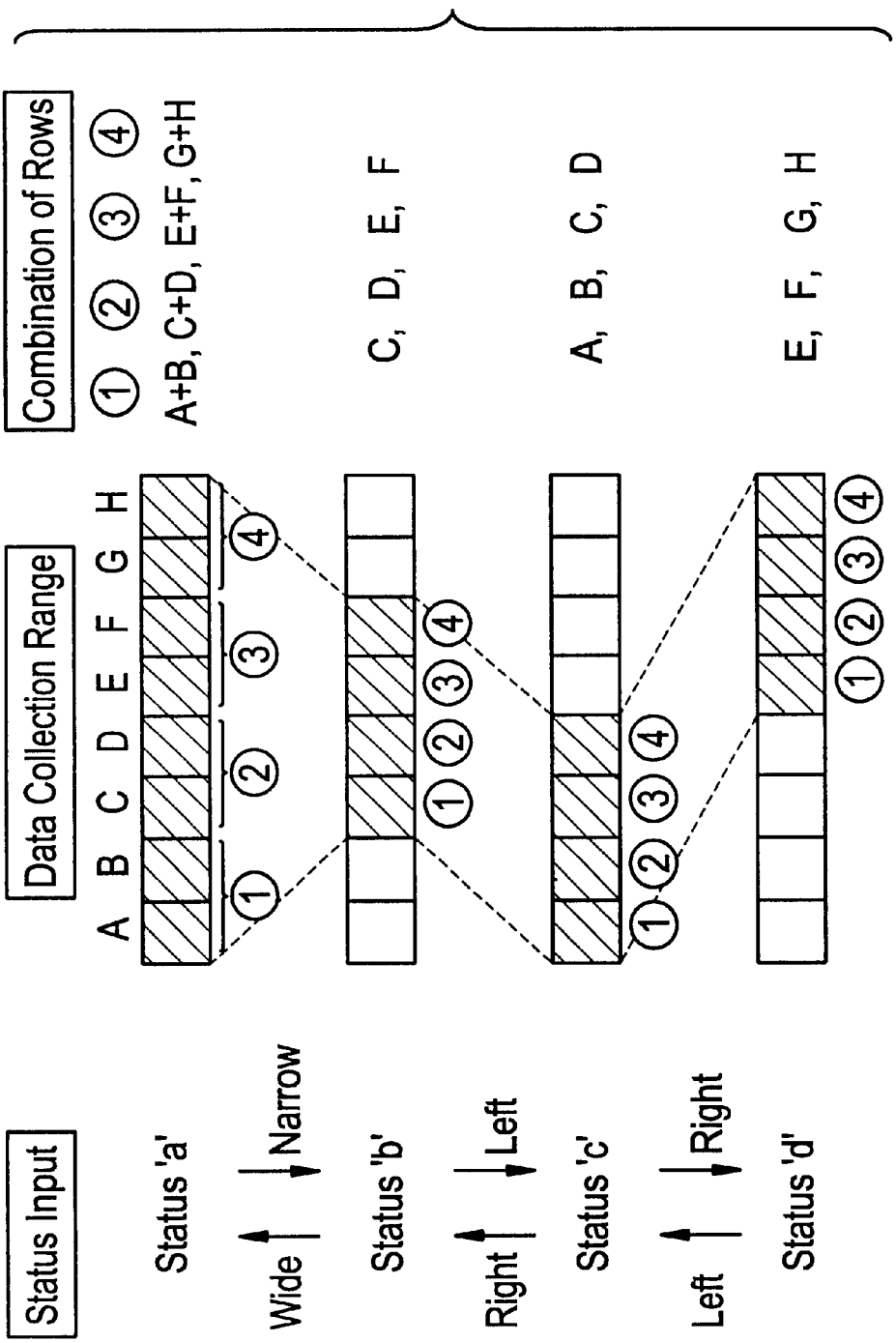
FIG. 6 exemplarily shows status information supplied from an input device, a data collection range in a selection/addition switching circuit in a data collecting section, and a combination of detector element rows in accordance with the first embodiment.

FIG. 6 exemplarily shows status information input via the input device 31, the data collection range in the selection/addition switching circuit 241 in the data collecting section 24, and a combination of the detector element rows.

The example shown in FIG. 6 is one in which the number of detector element rows is eight, i.e., the rows are A–H, and data of four rows are input to the ADC 242.

In the example shown in FIG. 6, status information 'a' prescribes data collection for a wide range, for example, for all the rows.

In this case, the selection/addition switching circuit 241 defines the rows A and B as a set ①, the rows C and D as a set ②, the rows E and F as a set ③ and the rows G and H as a set ④, and selects information of the sets ①–④ as the data for four rows.

The status information 'b' prescribes data collection for a narrower range, for example, for the four rows C–F in the central portion.

In this case, the selection/addition switching circuit 241 defines the row C as a set ①, the row D as a set ②, the row E as a set ③ and the row F as a set ④, and selects information of the sets ①–④ as the data for four rows.

In this example, when the status information 'b' is input under the status 'a', the selection/addition switching circuit 241 is commanded by the control signal CTL303 from the central processing apparatus 30 to perform data collection for the central four rows.

Moreover, when the status information 'a' is input under the status 'b', the selection/addition switching circuit 241 is commanded by the control signal CTL303 from the central processing apparatus 30 to perform data collection for all the rows.

The status information 'c' prescribes data collection for a narrow range, for example, for the four rows A–D toward the left in the drawing.

In this case, the selection/addition switching circuit 241 defines the row A as a set ①, the row B as a set ②, the row C as a set ③ and the row D as a set ④, and selects information of the sets ①–④ as the data for four rows.

In this example, when the status information 'c' is input under the status 'b', the selection/addition switching circuit 241 is commanded by the control signal CTL303 from the central processing apparatus 30 to perform data collection for the four rows on the left.

Moreover, when the status information 'b' is input under the status 'c', the selection/addition switching circuit 241 is commanded by the control signal CTL303 from the central processing apparatus 30 to perform data collection for the central four rows.

The status information 'd' prescribes data collection for a narrow range, for example, for the four rows E–H toward the right in the drawing.

In this case, the selection/addition switching circuit 241 defines the row E as a set ①, the row F as a set ②, the row G as a set ③ and the row H as a set ④, and selects information of the sets ①–④ as the data for four rows.

In this example, when the status information 'd' is input under the status 'c', the selection/addition switching circuit 241 is commanded by the control signal CTL303 from the central processing apparatus 30 to perform data collection for the four rows on the right.

Moreover, when the status information 'c' is input under the status 'd', the selection/addition switching circuit 241 is commanded by the control signal CTL303 from the central processing apparatus 30 to perform data collection for the four rows on the left.

Besides, the central processing apparatus 30 performs image reconstruction based on the data of a plurality of views collected at the data collecting section 24 as described above, produces a plurality of tomographic images in multi slice, and displays the images on the display device 32.

The image reconstruction at the central processing apparatus 30 employs, for example, a filtered backprojection technique.

The input device 31 is provided for inputting desired imaging conditions and the like, including the status information, to the central processing apparatus 30 by a human operator, and is comprised of a keyboard and a mouse, for example. The input device 31 may be connected to the scan gantry 2 or the imaging table 4.

The display device 32 displays the reconstructed images and other information supplied by the central processing apparatus 30.

The storage device 33 stores several kinds of data, reconstructed images and programs, and the stored data is accessed by the central processing apparatus 30 as necessary.

The operation in the aforementioned configuration will now be described with reference to FIG. 7.

Figure 7:
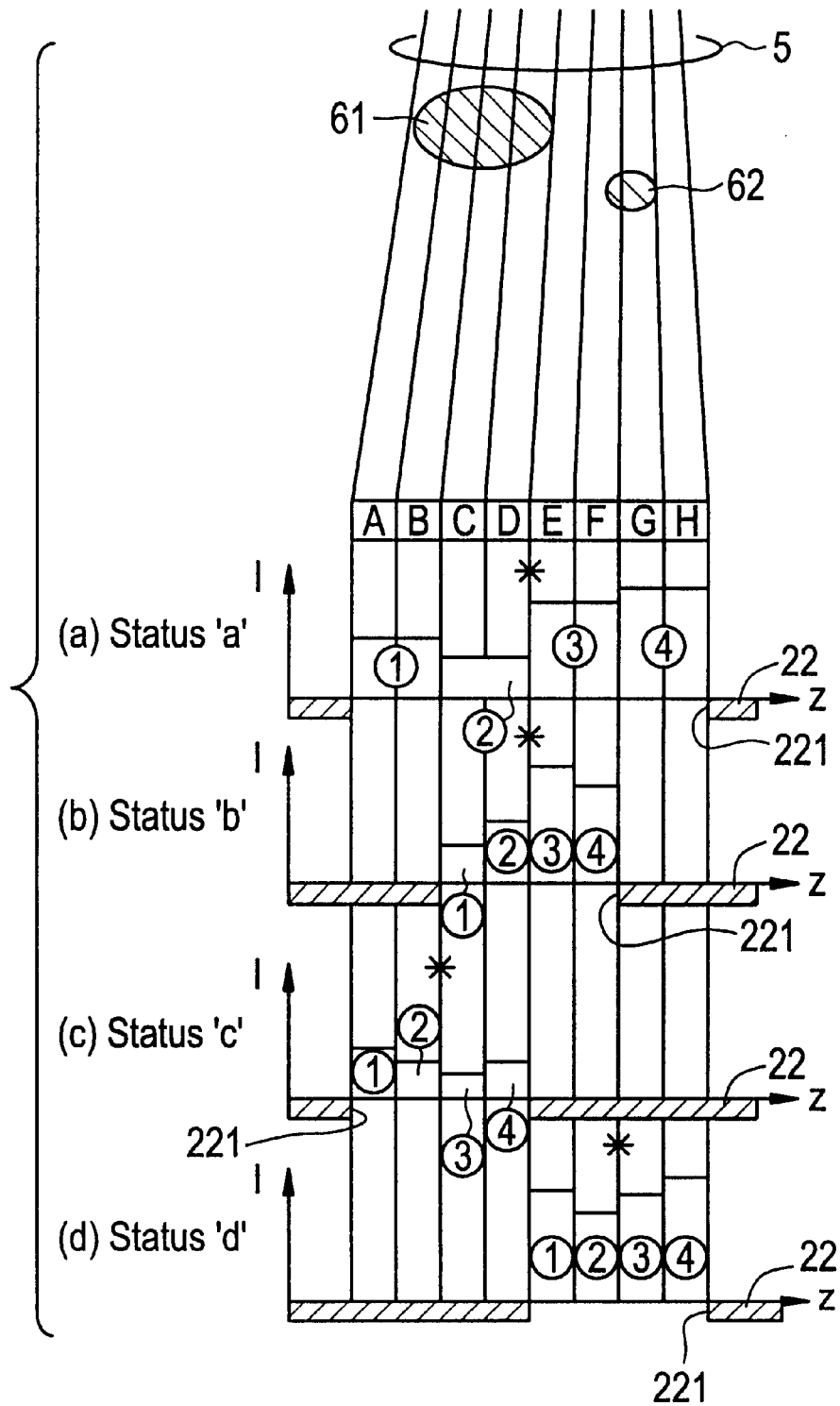
FIG. 7 is a diagram for explaining the operation of the first embodiment.

In FIG. 7, symbol I represents the intensity of signals input to the ADC 242 under the status 'a'–'d'; reference numeral 61 designates a large subject lying in the X-ray irradiated space 29, and 62 a smaller subject than the subject 61 lying in the X-ray irradiated space 29; and '*' represents the emission center of the X-ray tube 20.

First, the operator inputs information relating to a position to which the imaging table 4 is to move, to the central processing apparatus 30 via the input device 31.

The central processing apparatus 30 outputs the control signal CTL30b to the imaging table 4 for carrying the imaging table 4 for resting the subject 6 into and out of the X-ray irradiated space 29 in the scan gantry 2 in the z-direction, in response to the command input via the input device 31; performs fine adjustment and the like; and positions a desired site to be examined in the subject 6 at a desired position in the X-ray irradiated space 29 in the scan gantry 2.

Next, the central processing apparatus 30 is supplied with a start command of a multi-slice scan and status information via the input device 31. In this case, the status information 'a' is input to perform a gross scan using a large slice thickness in the beginning. The central processing apparatus 30 then outputs the control signal CTL301 to the X-ray controller 25. Based upon the signal, the X-ray controller 25 outputs the control signal CTL251 to the X-ray tube 20, and the X-ray tube 20 emits X-rays accordingly.

Moreover, the X-ray controller 25 outputs the control signal CTL252 to the X-ray tube moving section 21 to keep the X-ray tube 20 so that the emission center of the X-ray tube 20 is positioned at the center of the detector element array 23 in the z-direction, i.e., roughly on the boundary between the rows D and E, as shown in FIG. 7(a).

Then, the central processing apparatus 30 outputs the control signal CTL302 to the collimator controller 26, and the collimator controller 26 supplies the control signal CTL261 directing the driving section for the collimator 22 to adjust the openness of the aperture 221 so that all the rows A–H are irradiated with the X-ray beam 5.

Moreover, the central processing apparatus 30 outputs the control signal CTL303 to the selection/addition switching circuit 241. Accordingly, the selection/addition switching circuit 241 performs data collection on the signals detected by all the rows in the detector element array 23; defines the rows A and B as a set ①, the rows C and D as a set ②, the rows E and F as a set ③ and the rows G and H as a set ④; selects information of the sets ①–④ as the data for four rows; and supplies the data to the ADC 242.

The ADC 242 converts the analog signals from the selection/addition switching circuit 241 into digital signals, and outputs the converted signal to the central processing apparatus 30 as view data.

The central processing apparatus 30 performs image reconstruction based on the data for a plurality of views collected by the data collecting section 24, produces a plurality of tomographic images in multi slice, and displays the images on the display device 32.

Since the large subject 61 and the small subject 62 are contained in the imaged range in the tomographic images displayed on the display device 32, the images of the large and small subjects 61 and 62 are displayed with an intensity distribution as shown in FIG. 7(a).

When fluoro imaging, for example, is performed in this case, a needle is inserted to reach a desired site to be examined within the subject 6. If the needle is represented by, for example, the subject 61, the positional relationship between the needle and the site to be examined can be roughly known by inputting the status information 'a'.

Next, in order to ascertain the exact position with a reduced slice thickness, the status information 'b', for example, is input to the central processing apparatus 30 via the input device 31.

In this case, similarly to the above, the central processing apparatus 30 outputs the control signal CTL301 to the X-ray controller 25 so that the X-ray emission is performed with the emission center of the X-ray tube 20 positioned at the center of the detector element array 23 in the z-direction, i.e., positioned roughly on the boundary between the rows D and E, as shown in FIG. 7(b).

Then, the central processing apparatus 30 outputs the control signal CTL302 to the collimator controller 26, and the collimator controller 26 supplies the control signal CTL261 directing the driving section for the collimator 22 to adjust the openness of the aperture 221 so that the central four rows C–F are irradiated with the X-ray beam 5.

Moreover, the central processing apparatus 30 outputs the control signal CTL303 to the selection/addition switching circuit 241. Accordingly, the selection/addition switching circuit 241 performs data collection on the signals detected by the central four rows C–F among those detected by the detector element array 23; defines the row C as a set ①, the row D as a set ②, the row E as a set ③ and the row F as a set ④; selects information of the sets ①–④ as the data for four rows; and supplies the data to the ADC 242.

The ADC 242 converts the analog signals from the selection/addition switching circuit 241 into digital signals, and outputs the converted signal to the central processing apparatus 30 as view data.

The central processing apparatus 30 performs image reconstruction based on the data for a plurality of views collected by the data collecting section 24, produces a plurality of tomographic images in multi slice, and displays the images on the display device 32.

Since part of the large subject 61 and part of the small subject 62 are contained in the imaged range in the tomographic images displayed on the display device 32, the images of part of the large and small subjects 61 and 62 are displayed with an intensity distribution as shown in FIG. 7(*b*).

In this case, the positional relationship between the end portions of the subjects 61 and 62 can be more accurately known.

Next, when the exact position of the subject 61 is to be ascertained, the status information 'c', for example, is input to the central processing apparatus 30 via the input device 31.

In this case, the central processing apparatus 30 outputs the control signal CTL301 to the X-ray controller 25 so that the X-ray emission is performed with the emission center of the X-ray tube 20 positioned at the portion of the detector element array 23 toward the z-direction, i.e., positioned roughly on the boundary between the rows B and C, as shown in FIG. 7(*c*).

Then, the central processing apparatus 30 outputs the control signal CTL302 to the collimator controller 26, and the collimator controller 26 supplies the control signal CTL261 directing the driving section for the collimator 22 to adjust the openness of the aperture 221 so that the four rows A–D toward one side are irradiated with the X-ray beam 5.

Moreover, the central processing apparatus 30 outputs the control signal CTL303 to the selection/addition switching circuit 241. Accordingly, the selection/addition switching circuit 241 performs data collection on the signals detected by the four rows A–D toward the left in FIG. 7 among those detected by the detector element array 23; defines the row A as a set ①, the row B as a set ②, the row C as a set ③ and the row D as a set ④; selects information of the sets ①–④ as the data for four rows; and supplies the data to the ADC 242.

The ADC 242 converts the analog signals from the selection/addition switching circuit 241 into digital signals, and outputs the converted signal to the central processing apparatus 30 as view data.

The central processing apparatus 30 performs image reconstruction based on the data for a plurality of views collected by the data collecting section 24, produces a plurality of tomographic images in multi slice, and displays the images on the display device 32.

Since only the large subject 61 is contained in the imaged range in the tomographic images displayed on the display device 32, an overview of the subject 61 is displayed with an intensity distribution as shown in FIG. 7(*c*).

In this case, the positional relationship in the subject 61 can be more accurately known.

Next, when the exact position of the subject 62 is to be ascertained, the status information 'd', for example, is input to the central processing apparatus 30 via the input device 31.

In this case, the central processing apparatus 30 outputs the control signal CTL301 to the X-ray controller 25 so that the X-ray emission is performed with the emission center of the X-ray tube 20 positioned at the portion of the detector element array 23 toward the z-direction, i.e., positioned roughly on the boundary between the rows F and G, as shown in FIG. 7(*d*).

Then, the central processing apparatus 30 outputs the control signal CTL302 to the collimator controller 26, and the collimator controller 26 supplies the control signal CTL261 directing the driving section for the collimator 22 to adjust the openness of the aperture 221 so that the four rows E–H toward one side are irradiated with the X-ray beam 5.

Moreover, the central processing apparatus 30 outputs the control signal CTL303 to the selection/addition switching circuit 241. Accordingly, the selection/addition switching circuit 241 performs data collection on the signals detected by the four rows E–H toward the right in FIG. 7 among those detected by the detector element array 23; defines the row E as a set ①, the row F as a set ②, the row G as a set ③ and the row H as a set ④; selects information of the sets ①–④ as the data for four rows; and supplies the data to the ADC 242.

The ADC 242 converts the analog signals from the selection/addition switching circuit 241 into digital signals, and outputs the converted signal to the central processing apparatus 30 as view data.

The central processing apparatus 30 performs image reconstruction based on the data for a plurality of views collected by the data collecting section 24, produces a plurality of tomographic images in multi slice, and displays the images on the display device 32.

Since only the small subject 62 is contained in the imaged range in the tomographic images displayed on the display device 32, an overview of the subject 62 is displayed with an intensity distribution as shown in FIG. 7(*d*).

In this case, the positional relationship in the subject 62 can be more accurately known.

As described above, according to the first embodiment, there are provided the X-ray tube 20 for emitting X-rays; the X-ray tube moving section 21 capable of moving the emission center of the X-ray tube 20 in a direction of carrying the imaging table 4 for resting the subject into and out of the X-ray irradiated space 29 in the scan gantry 2 (i.e., z-direction); the collimator 22 having an aperture whose openness can be adjusted, for forming the X-rays emitted by the X-ray tube 20 into the fan-shaped X-ray beam 5 having a certain width and a certain thickness (slice thickness) to irradiate a desired region on the detector element array 23 with the X-ray beam 5; the data collecting section 24 for dynamically selecting or adding in varying combination the detected signal input supplied from the detector element rows in the detector element array 23 during scanning in response to the control signal CTL303; and a central processing apparatus 30 for changing the emission center of the X-ray tube 20, the openness of the aperture in the collimator 22, and the data to be collected by the data collecting section 24 in response to the status information input via the input device 31; and therefore the slice thickness can be dynamically switched during scanning.

Moreover, the focus of the radiation can be arbitrarily moved in a direction of carrying the subject, and hence an advantage that tomographic imaging can be performed with safety and high accuracy can be obtained.

Especially, since the slice thickness can be dynamically switched during scanning, when, for example, fluoro imaging is performed in which a needle is inserted into the subject 6 for imaging, the slice thickness can be increased first to roughly guide the position of the needle, and the slice thickness can be decreased last to indicate an exact position. Therefore, when the position of the subject 6 is shifted due to the body motion or the like, a correction can be easily made in the z-direction (in the body axis direction) without moving the cradle.

Consequently, the tomographic imaging can be performed with safety and high accuracy.

Second Embodiment

Figure 8:
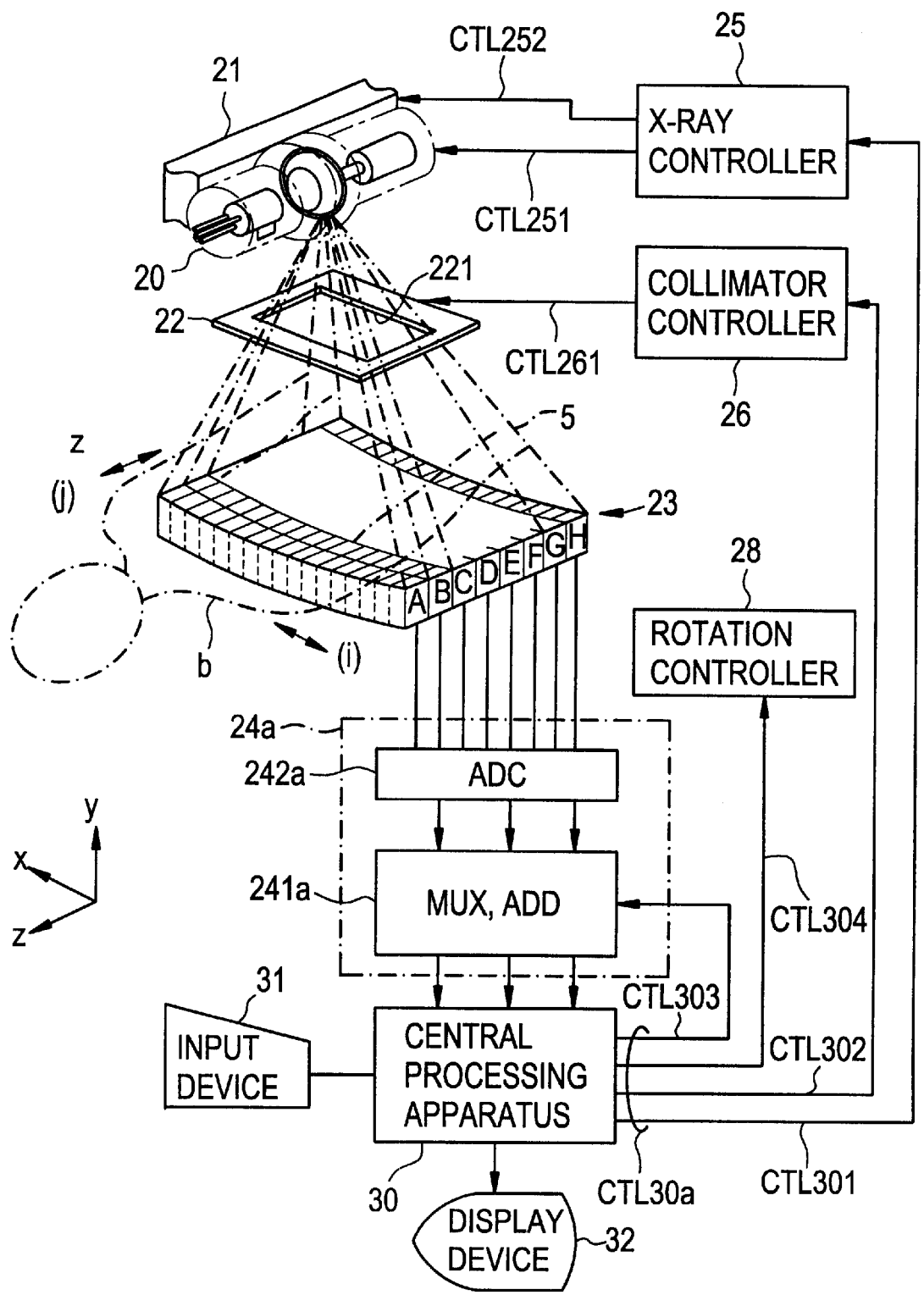
FIG. 8 is a system configuration diagram showing a second embodiment of the main portion of an X-ray CT apparatus that serves as the radiation tomographic imaging apparatus in accordance with the present invention.

FIG. 8 is a system configuration diagram showing a second embodiment of the main portion of an X-ray CT apparatus that serves as the radiation tomographic imaging apparatus in accordance with the present invention.

The difference between the second embodiment and the first embodiment is in a data collecting section 24a. Specifically, the data collecting section 24a is configured so that the signals detected at the detector element array 23 are first converted into digital data at an ADC 242a, and then the digital detected signals from the detector element rows (e.g., eight rows A–H) in the detector element array 23 are dynamically selected or added in varying combination, in response to the control signal CTL303 from the central processing apparatus 30.

Other configuration and operation are the same as those in the first embodiment.

According to the second embodiment, the same effects as those in the first embodiment can be obtained.

Third Embodiment

Figure 9:
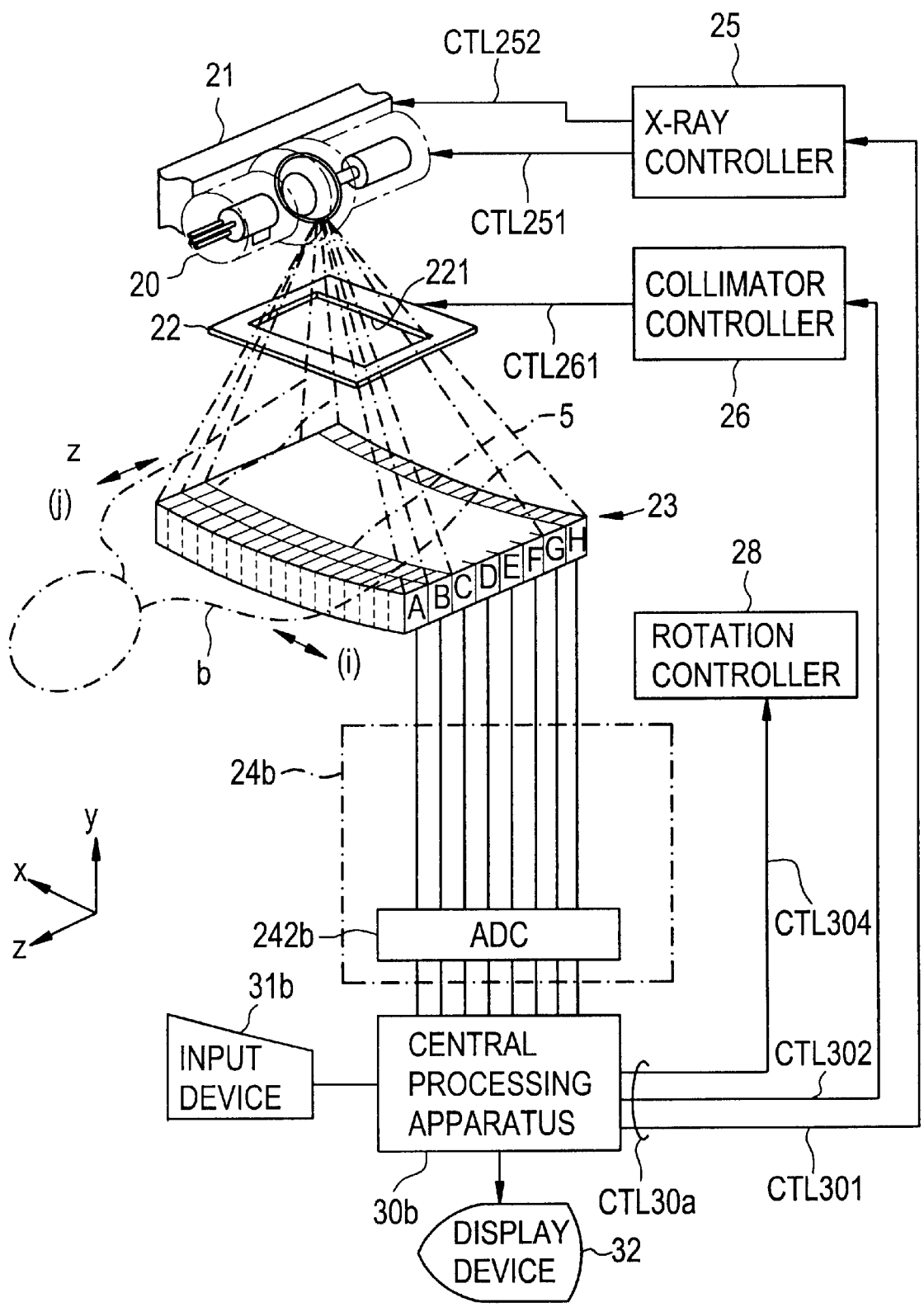
FIG. 9 is a system configuration diagram showing a third embodiment of the main portion of an X-ray CT apparatus that serves as the radiation tomographic imaging apparatus in accordance with the present invention.

FIG. 9 is a system configuration diagram showing a third embodiment of the main portion of an X-ray CT apparatus that serves as the radiation tomographic imaging apparatus in accordance with the present invention.

The difference between the third embodiment and the first embodiment is in a data collecting section 24b. Specifically, only an ADC 242b is provided in the data collecting section 24b, and the digital detected signals from the detector element rows (e.g., eight rows A–H) in the detector element array 23 are directly input to a central processing apparatus 30b. In the central processing apparatus 30b, reconstruction parameters are dynamically varied according to an input via the input device 31 to change the slice thickness and the reconstruction position in the z-direction.

Other configuration and operation are the same as those in the first embodiment.

According to the third embodiment, the same effects as those in the first embodiment can be obtained.

Although the description has been made on a case in which X-rays are employed as the radiation in the preceding embodiments, the radiation is not limited to X-rays but may be any other type of radiation such as γ-rays. However, X-rays are presently preferred because various practical means for their generation, detection, control and the like are best developed and widely available.

Many widely different embodiments of the invention may be configured without departing from the spirit and the scope of the present invention. It should be understood that the present invention is not limited to the specific embodiments described in the specification, except as defined in the appended claims.

What is claimed is:

1. A radiation tomographic imaging apparatus comprising:

a radiation tube for emitting radiation;

a collimator capable of forming said radiation emitted by said radiation tube into a radiation beam to emit said radiation beam and capable of changing a range irradiated by said radiation beam in response to a first control signal;

a detector element array comprising a plurality of radiation detector elements with irradiated surfaces thereof facing in an impinging direction of said radiation beam, wherein an array of said radiation detector elements are arranged in one of two mutually perpendicular directions to form a detector element row; and wherein a plurality of said detector element rows are arranged side by side in another of said two mutually perpendicular directions;

moving means for moving an emission center of said radiation tube in said another of said two mutually perpendicular directions in response to a second control signal;

control means for receiving radiation irradiated range information and for outputting said first control signal to said collimator and said second control signal to said moving means corresponding to said information; and image producing means for producing multi-slice tomographic images of a region through which said radiation beam passes based on radiation detected signals for a plurality of views detected by said detector element array corresponding to said irradiated range information.

2. The apparatus of claim 1, further comprising: rotating means for rotating said radiation tube, collimator and detector element array around a subject disposed in a radiation irradiated space.

3. The apparatus of claim 2, further comprising display means for displaying tomographic images produced by said image producing means.

4. The apparatus of claim 1, further comprising:

data collecting means for collecting desired data by selecting or combining detected signals from said detector element rows in said detector element array in response to a third control signal; and wherein said control means controls said third control signal as supplied to said data collecting means; and wherein said detected signal includes signals collected by said data collecting means.

5. The apparatus of claim 4, wherein said data collecting means comprises:

switching means for causing collecting of desired data by selecting or combining detected signals from said detector element rows in said detector element array in response to said third control signal; and converter means for converting data from said switching means operation into digital data and for outputting said digital data to said image producing means.

6. The apparatus of claim 4, wherein said data collecting means comprises:

converter means for converting detected signals from said detector element rows in said detector element array into digital data; and switching means for causing collecting of desired data by selecting or combining said digital data from said converter means in response to said third control signal, and for outputting said desired data to said image producing means.

7. A radiation tomographic imaging method comprising the steps of:

emitting radiation using a radiation tube;

forming radiation emitted by said radiation tube into a radiation beam to emit said radiation beam and changing a range irradiated by said radiation beam in response to a first control signal;

applying said radiation beam to a detector element array comprising a plurality of radiation detector elements with irradiated surfaces thereof facing in an impinging direction of said radiation beam, wherein an array of said radiation detector elements are arranged in one of two mutually perpendicular directions to form a detector element row, and wherein a plurality of said detector element rows are arranged side by side in another of said two mutually perpendicular directions;

moving an emission center of said radiation tube in another of said two mutually perpendicular directions in response to a second control signal;

generating said first control signal and said second control signal in response to said irradiated range information; and producing multi-slice tomographic images of a region through which said radiation beam passes based on radiation detected signals for a plurality of views detected by said detector element array corresponding to said irradiated range information.

8. The method of claim 7, further comprising the step of rotating said radiation tube, and detector element array around a subject disposed in a radiation irradiated space.

9. The method of claim 8, further comprising the step of displaying tomographic images.

10. The method of claim 7, further comprising the steps of:

collecting desired data by selecting or combining detected signals from said detector element rows in said detector element array in response to a third control signal; and supplying said third control signal; wherein said detected signals include said desired data.

11. The method of claim 10, further comprising the step of:

converting said desired data into digital data and using said digital data to produce said tomographic images.

12. The method of claim 7, further comprising the steps of:

converting detected signals from said detector element array into digital data;

collecting desired data by selecting or combining said digital data; and using said desired data to produce said tomographic images.

13. A radiation tomographic imaging apparatus comprising:

first means for emitting radiation beam and for changing a range irradiated by said radiation beam in response to a first control signal;

a detector element array comprising a plurality of radiation detector elements with irradiated surfaces thereof facing in an impinging direction of said radiation beam, wherein said plurality of detector elements are arranged in one of two mutually perpendicular directions to form a detector element row, and wherein a plurality of said detector element rows are arranged side by side in another of said two mutually perpendicular directions;

moving means for moving an emission center of said first means in another of said two mutually perpendicular directions in response to a second control signal;

second means for producing said first control signal and said second control signal in response to irradiated range information from said first means and for outputting said first control signal to said first means and said second control signal to said moving means; and third means for producing multi-slice tomographic images of a region through which said radiation beam passes based on radiation detected signals for a plurality of views detected by said detector element array corresponding to said irradiated range information.

14. The apparatus of claim 13, further comprising:

means for rotating said first means and said detector element array around a subject disposed in a radiation irradiating space.

15. The apparatus of claim 14, further comprising:

means for displaying said tomographic images.

16. The apparatus of claim 13, further comprising:

fourth means for collecting desired data by selecting or combining detected signals from said detector element row in said detector element array in response to said second control signal;

and wherein said second means controls said second control signal;

and wherein said detected signal includes signals collected by said fourth means.

17. The apparatus of claim 16, wherein said fourth means comprises:

means for collecting desired data by selecting or combining detected signals from said detector element rows in response to said second control signals; and means for converting data from said means for collecting into digital data and for outputting said digital data to said third means.

18. The apparatus of claim 16, wherein said fourth means comprises:

means for converting detected signals from said detector element rows into digital data; and means for collecting desired data by selecting or combining said digital data in response to said second control signal and for outputting data to said third means.

* * * * *